United States Patent
Mager et al.

(10) Patent No.: US 9,109,943 B2
(45) Date of Patent: Aug. 18, 2015

(54) WEIGHT-SENSING SURFACES WITH WIRELESS COMMUNICATION FOR INVENTORY TRACKING

(75) Inventors: Michael J. Mager, San Diego, CA (US); John D. Boyd, San Diego, CA (US); Bennett M. King, San Diego, CA (US); Geoffrey C. Wenger, San Diego, CA (US); James B. Cary, San Diego, CA (US)

(73) Assignee: QUALCOMM Incorporated, San Diego, CA (US)

( * ) Notice: Subject to any disclaimer, the term of this patent is extended or adjusted under 35 U.S.C. 154(b) by 679 days.

(21) Appl. No.: 13/399,322

(22) Filed: Feb. 17, 2012

(65) Prior Publication Data

US 2013/0218511 A1 Aug. 22, 2013

(51) Int. Cl.
  *G06F 19/00* (2011.01)
  *G01G 23/37* (2006.01)
  *G06F 11/30* (2006.01)

(52) U.S. Cl.
  CPC ........ *G01G 23/3735* (2013.01); *G06F 19/3475* (2013.01)

(58) Field of Classification Search
  CPC .................. G09F 19/3475; G01G 23/3735
  USPC ....................................... 702/129
  See application file for complete search history.

(56) References Cited

U.S. PATENT DOCUMENTS

| | | | |
|---|---|---|---|
| 6,204,763 B1 * | 3/2001 | Sone | 340/568.1 |
| 2002/0161652 A1 | 10/2002 | Paullin et al. | |
| 2004/0238228 A1 | 12/2004 | Montague et al. | |
| 2005/0060246 A1 | 3/2005 | Lastinger et al. | |
| 2005/0171854 A1 | 8/2005 | Lyon | |
| 2006/0036395 A1 * | 2/2006 | Shaya et al. | 702/127 |
| 2010/0049471 A1 | 2/2010 | Gage et al. | |
| 2010/0109876 A1 | 5/2010 | Schmid-Schonbein et al. | |
| 2011/0282726 A1 * | 11/2011 | Brown et al. | 705/14.35 |

FOREIGN PATENT DOCUMENTS

| | | |
|---|---|---|
| JP | 2005342272 A | 12/2005 |
| WO | WO 2006116665 A1 | 11/2006 |

OTHER PUBLICATIONS

International Search Report and Written Opinion—PCT/US13/26482—ISA/EPO—Mar. 27, 2014.

* cited by examiner

*Primary Examiner* — Phuong Huynh
(74) *Attorney, Agent, or Firm* — Jeffrey D. Jacobs

(57) ABSTRACT

Methods, systems, and devices are described for identifying and determining quantity data for consumable items from a plurality of weight sensing devices. A consumption metric for the consumable items is determined based on the identification and quantity data. Consumption-related information is provided based on the consumption metric. Consumption-related information may be used for a number of purposes, including for providing aggregate consumption information to suppliers, and health advice and recipes to users, for example.

48 Claims, 14 Drawing Sheets

WEIGHT-SENSING SURFACES WITH WIRELESS COMMUNICATION FOR INVENTORY TRACKING

BACKGROUND

The following relates generally to identifying and monitoring quantities of consumable items, and more specifically to identification of consumption metrics associated with one or more consumable items and the generation of information related to the consumption metrics.

Consumable items are ubiquitous in residential, commercial, and industrial settings. In a residential setting, consumable items commonly include food items and health items such as medications, toothpaste, etc. Accurate inventory and monitoring of consumable items may assist a consumer in making a number of decisions, such as, for example, replenishing any depleted or nearly depleted items, selecting one or more items for a meal, and monitoring intake of various items. For example, information related to items in a consumer's refrigerator and/or pantry may be useful to a consumer in meal planning, identifying items needed from a store, etc. Additionally, information related to recent and historical consumption of items may be useful to determine intake of substances, such as sodium or sugars, and identify if consumption of any particular item should be increased or decreased based on recent and/or historical consumption information.

Information related to consumption as described above may be useful for entities other than individual consumers as well. For example, suppliers, manufacturers, and distributors of items may find information related to consumption of various items useful for business or advertising purposes. Health care providers may also use information related to consumption of items for health monitoring purposes. Safe and secure collection of such information, aggregation of such information, and delivery of such information would thus be beneficial.

SUMMARY

The described features generally relate to one or more improved systems, methods, and/or apparatuses for identifying and determining quantity data for consumable items from a plurality of weight sensing devices, determining a consumption metric for the consumable items, and generating consumption-related information based on the consumption metric. Consumption-related information may be used for a number of purposes, including for providing aggregate consumption information to suppliers, health advice, and recipes, for example.

In one example, novel functionality is described for using identification and quantity data for consumable items to generate consumption-related information. Identification and quantity data for one or more consumable items are received from a number of weight sensing devices that determine identification and quantity data based on the weight of the item on the weight sensing device. A consumption metric for the one or more consumable items is determined based on the received data, and consumption-related information is generated based on the consumption metric. In one example, the number of weight sensing devices are associated with different users, and the consumption metric comprises an aggregate consumption metric for the one or more consumable items based on the received information from the number of different users. Such consumption-related information may include, for example, supply chain distribution information for use in providing sufficient supply for replenishment of the one or more consumable items for the number of users. In other examples, the consumption-related information may include one or more recipes for a specific user based on the user's consumption metric for the one or more consumable items, and/or health advice for a specific user such as a warning to the user indicating that the user's consumption of one or more consumable items exceeds a predetermined difference from a target threshold.

In one example, a method includes: receiving, at a computer system, identification and quantity data for one or more consumable items from a number of weight sensing devices remote from the computer system, determining a consumption metric for the one or more consumable items based on the received data, and generating consumption-related information based on the consumption metric. The number of weight sensing devices may be associated with a number of different users, and determining a consumption metric may include determining an aggregate consumption metric for the one or more consumable items based on the received information from the number of different users. Generating consumption-related information may include generating supply chain distribution information for use in providing sufficient supply for replenishment of the one or more consumable items for the number of users. The number of users may include one or more of: a defined geographic area, a defined demographic, a defined interest group, and a defined social network. In some examples, the consumption-related information includes one or more recipes based on the consumption metric for the one or more consumable items. In other examples, the consumption-related information comprises health advice for a user of a weight sensing surface such as a warning to the first user indicating that consumption of one or more consumable items exceeds a predetermined difference from a target threshold. In further examples, generating consumption-related information includes generating a coupon for a user associated with a weight sensing surface for one or more consumable items consumed by the user. Generating consumption-related information may also include, in some examples, providing a directed advertisement to a user associated with a weight sensing surface based on the consumption metric for one or more consumable items consumed by the user.

The receiving identification and quantity data may include periodically receiving identification and quantity data, and determining a consumption metric may be based on differences in quantity data over time, and/or be based on a rate of depletion of a consumable item. Determining a consumption metric may be based on an average rate of depletion of the first consumable item across a number of replenishments of the first consumable item.

The generating of consumption-related information based on the consumption metric according to an example may include generating a replenishment notice to a user indicating that one or more consumable items are depleted or approaching depletion. In other examples, generating consumption-related information based on the consumption metric includes determining that quantity data for one or more consumable items is below a quantity threshold associated with the consumable item, and generating the replenishment notice. The consumption metric may include a rate of consumption for a consumable item, and generating a replenishment notice may include determining, based on the rate of consumption, that the consumable item is forecast to be depleted within a preset time period, and generating the replenishment notice. The preset time period for the consumable item may be selectable by a user.

In one example, an apparatus is provided that includes: a collector module that receives identification and quantity data for one or more consumable items from a number of remote weight sensing surfaces and determines a consumption metric for the one or more consumable items, and a consumption-related information generator module that generates consumption-related information based on the consumption metric. The collector module may determine an aggregate consumption metric for the one or more consumable items based on the received information from the number of users. The consumption-related information generator, in an example, provides supply chain distribution information for use in providing sufficient supply of the one or more consumable items for the number of users based on the aggregate consumption metric. The number of users may include users within one or more of: a defined geographic area, a defined demographic, a defined interest group, and a defined social network.

In some examples, the consumption-related information includes one or more recipes based on the consumption metric for the one or more consumable items. In other examples, the consumption-related information includes health advice for a first user of a first weight sensing surface. Such health advice may include, for example, a warning indicating that consumption of one or more consumable items exceeds a predetermined difference from a target threshold. The consumption-related information may include, in further examples, a coupon for a first user associated with a first weight sensing surface for one or more consumable items consumed by the first user. The consumption-related information comprises a directed advertisement to a first user associated with a first weight sensing surface based on the consumption metric for one or more consumable items consumed by the first user.

In various examples, the collector module receives periodic updates of identification and quantity data for the one or more consumable items, and determines the consumption metric based on a rate of depletion of the one or more consumable items. In such examples, the consumption metric may be determined based on an average rate of depletion of one or more first consumable items across a plurality of replenishments of the one or more consumable items. The consumption-related information generator, in some examples, provides a replenishment notice to a user of a weight sensing surface indicating that one or more consumable items are depleted or approaching depletion. The consumption metric may comprise a rate of consumption for a consumable item, and the consumption-related information generator may determine, based on the rate of consumption, that the consumable item is forecast to be depleted within a preset time period, and generate the replenishment notice.

In one example, a system includes: means for receiving identification and quantity data for one or more consumable items from a number of weight sensing means remote from the means for receiving; means for determining a consumption metric for the one or more consumable items based on the received data; and means for generating consumption-related information based on the consumption metric. The number of weight sensing means may be associated with a number of different users, and the means for determining a consumption metric may include means for determining an aggregate consumption metric for the one or more consumable items based on the received information from the number of different users. The means for generating consumption-related information, according to an example, includes means for generating supply chain distribution information for use in providing sufficient supply for replenishment of the one or more consumable items for the number of users. The number of users may include users within one or more of: a defined geographic area, a defined demographic, a defined interest group, and a defined social network. In some examples, the means for receiving identification and quantity data includes means for periodically receiving identification and quantity data, and the means for determining a consumption metric includes means for determining a consumption metric based on differences in quantity data over time.

In another example, a computer program product is provided that includes a non-transitory computer readable medium comprising: code for receiving, at a computer system, identification and quantity data for one or more consumable items from a number of weight sensing devices remote from the computer system, code for determining a consumption metric for the one or more consumable items based on the received data, and code for generating consumption-related information based on the consumption metric. The number of weight sensing devices are associated with a number of different users, and the code for determining a consumption metric may include code for determining an aggregate consumption metric for the one or more consumable items based on the received information from the number of different users. The code for generating consumption-related information may include code for generating supply chain distribution information for use in providing sufficient supply for replenishment of the one or more consumable items for the number of users. In some examples, the number of users comprise users within one or more of: a defined geographic area, a defined demographic, a defined interest group, and a defined social network. The code for generating consumption-related information may include code for generating a coupon for a first user associated with a first weight sensing surface for one or more consumable items consumed by the first user. The code for generating consumption-related information may, in other examples, include code for providing a directed advertisement to a first user associated with a first weight sensing surface based on the consumption metric for one or more consumable items consumed by the first user. The code for receiving identification and quantity data may include, according to various examples, code for periodically receiving identification and quantity data, and the code for determining a consumption metric may include code for determining a consumption metric based on differences in quantity data over time. In some examples, the code for receiving identification and quantity data includes code for periodically receiving identification and quantity data for a first consumable item, and the code for determining a consumption metric may include code for determining a consumption metric based on a rate of depletion of the first consumable item.

BRIEF DESCRIPTION OF THE DRAWINGS

A further understanding of the nature and advantages of the present invention may be realized by reference to the following drawings. In the appended figures, similar components or features may have the same reference label. Further, various components of the same type may be distinguished by following the reference label by a dash and a second label that distinguishes among the similar components. If only the first reference label is used in the specification, the description is applicable to any one of the similar components having the same first reference label irrespective of the second reference label.

DETAILED DESCRIPTION

Figure 1:
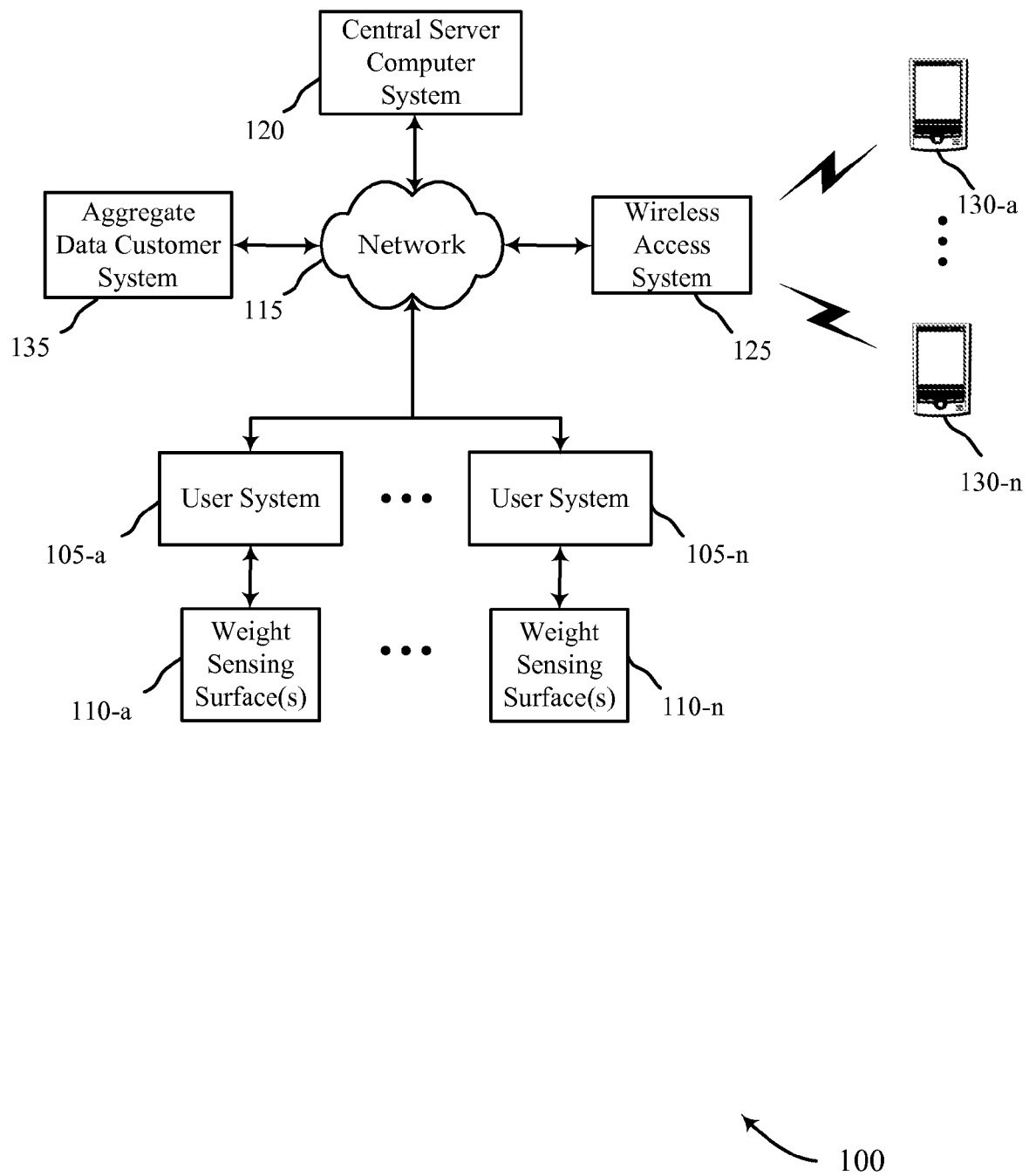
FIG. 1 shows a block diagram of an example of a system of the disclosure.

Systems are provided to determine an inventory of consumable items, determine a consumption metric related to the consumable items, and provide consumption-related information based on the consumption metric. Consumable items may include food or health related products, for example, and the consumption metric may include a quantity of the consumable items present or consumed by a consumer or in a household. A user, such as an individual or household, may have a user system to report information related to consumable items and quantity data associated with the consumable items. Such a user system may include one or more weight sensing surfaces that can identify an item and determine quantity data related to the item based on an item weight detected by the weight sensing surface(s).

Consumption-related information may be determined by identifying an item and a weight of the item, and differences in item weight over time. Consumption-related information may in some cases include aggregate consumption information for a group of users, which may be used for any of a number of purposes, such as supply chain management to ensure sufficient inventories of a product in a certain geographic area based on aggregate consumption information for a group of users in the geographic area, and advertising directed to the group of users, for example. In some examples, consumption-related information may include times of consumption of items, which may be used, for example, by advertisers interested to know when items tend to be consumed, such as increased alcoholic beverage or soft drink consumption during certain sporting events or television shows. Consumption-related information may also include health related information, such as a warning about quantities of certain items (e.g. sodium) that have been consumed or a warning about late-night or non-mealtime snacking. In various examples, systems may provide suggested recipes, coupons, advertising, warnings, articles, and/or other information to users based on consumption and/or inventory information. Information may be provided to a consumer, a corporate user such as advertiser or supplier, and/or a governmental or other entity that seeks to collect aggregate information related to one or more items, or consumption patterns for one or more groups of users. Privacy safeguards may be implemented to prevent unique consumer data from being provided absent permission from the particular consumer.

Thus, the following description provides examples, and is not limiting of the scope, applicability, or configuration set forth in the claims. Changes may be made in the function and arrangement of elements discussed without departing from the spirit and scope of the disclosure. Various examples may omit, substitute, or add various procedures or components as appropriate. For instance, the methods described may be performed in an order different from that described, and various steps may be added, omitted, or combined. Also, features described with respect to certain examples may be combined in other examples.

Referring first to FIG. 1, a block diagram illustrates an example of a system 100 that includes a number of user systems 105. A user system 105 is connected to one or more weight sensing surfaces 110. The weight sensing surfaces 110 may include components to identify items placed on the surface, as well as a weight of the item. For example, and as will be described in more detail below, a weight sensing surface 110 may include one or more Radio Frequency Identification (RFID) interrogators that are able to read RFID tags that are located on consumable items. The RFID interrogators are also able to determine a location of the consumable items on the weight sensing surface 110. The weight sensing surfaces 110 may also be able to determine a weight of the item, which may be used to determine quantity data related to the item. The identification and quantity data may be sent over network 115 to a central server computer system 120. In some examples, RFID interrogators read a URL from an item's RFID tag and retrieve item information via network 115 from a remote server associated with the manufacturer of the item. In such cases, a manufacturer may provide an item's original weight and contents, and also provide updates to item information, such as adding recall notices. The user systems 105 each may include a number of weight sensing surfaces 110 located in different areas, such as in a refrigerator, in a pantry, and/or in a medicine cabinet, for example. Each weight sensing surface 110 may operate to communicate with network 115 through a network connection, a wireless connection (e.g., a IEEE 802.11, Zigbee™, Bluetooth™ connection, or other wireless standard), or may otherwise connect to a central node in a user system 105 that then communicates over network 115.

The central server computer system 120 may, for example, be made up one or more server computers, personal computers, workstations, web servers, or other suitable computing devices, and the individual computing device(s) for a given server may be local or remote from each other. The central server computer system 120 may collect item and quantity data and provide various consumption-related information based on the collected data. For example, central server computer system 120 may receive identifying data from RFID tags and determine a particular item associated with the RFID tag based on the identifying data. A bag of sugar, for example, located on weight sensing surface 110-a may have an RFID tag that reports an identification code upon interrogation by an RFID interrogator. The weight sensing surface 110-a may provide a weight of the bag, along with the identification code, which is used by the central server computer system to determine that the identification code indicates that the item is sugar. The central server computer system 120 may also determine the weight of a full bag of sugar and determine a quantity of sugar present in the reported container. In other examples, the determination that the item is a bag of sugar and of the weight of a full bag of sugar may be accomplished by accessing a URL reported by the RFID tag on the item. In some examples, the user system 105 queries the central server computer system 120 to determine item identification and full weight of the item, with an inventory of all items maintained by the user system 105. The user system 105 in such examples may periodically report information to the central server computer system 120 related to item inventory and consumption data.

Information may be reported back to a user of the user system 105-a through an interface in user system 105-a, through a wireless access system 125 and mobile devices 130, and/or through a user-accessible web-based interface. In such a system a user of user system 105-a may have a mobile device 130-a that is used to monitor items that are located on weight sensing surface(s) 110-a and access consumption-related information. Such information, as will be described in more detail below, may be used to determine shopping lists or recipes, for example. A mobile device 130 may be one of a number of devices, such as a smartphone, a cellular phone, a VoIP phone, a personal digital assistant, a tablet computer, a laptop computer, a portable digital music player, or other mobile device that communicates voice and/or data, or any combination of the foregoing. A web-based interface may also be provided that a user may access from any web-enabled device to monitor and manage inventory, recipes, alerts, and user settings. The wireless access system 125 may include any suitable wireless network capable of transmitting data on any of a number of different wireless protocols. Such networks are well known and need not be described in further detail here.

Consumption information may also be provided to an aggregate data customer system 135, for use by an entity interested in aggregated consumption-related information. Consumption-related information may be provided that is aggregated information related to a group of user systems 105, such as all user systems 105 located in a particular geographic area, user systems 105 associated with users having a particular common interest (e.g., runners, car enthusiasts, or members of a social network), or user systems 105 associated with a particular demographic, to name a few.

The aggregate data customer system 135 in some examples may use such information to adjust a supply chain or distribution for consumable items. If the aggregate data customer system 135 is used by a grocery distributor, for example, aggregate data indicating that people in a particular geographic area have an abundance of eggs may lead the distributor to reduce the number of eggs requested from their egg supplier and reduce the number of eggs provided to grocery stores in that particular geographic area. Likewise, if aggregate data indicates people in a particular geographic area are low on eggs as a group, the distributor may increase the number of eggs requested from their egg supplier and increase the number of eggs provided to grocery stores in that particular geographic area in anticipation of an imminent increase in demand. Similarly, if the aggregate data customer system 135 is used by an advertising agency, aggregate data indicating that people of a particular demographic or group tend to consume particular items in relatively large quantities may prompt an advertising or coupon campaign directed to that demographic or group. For example, if car enthusiasts tend to consume relatively large quantities of beef, a beef supplier may decide to increase advertising in media known to be popular to car enthusiasts. Additionally, if the aggregate data customer system 135 is used by an advertising agency, aggregate data indicating consumption times that people of a particular demographic or group tend to consume particular items in relatively large quantities may prompt an advertising or coupon campaign directed to media viewed by consumers during such high-consumption times. In various examples, users of user systems 105 may elect to provide information related their interests, social groups, and/or demographic information, and make this information available to aggregate data customer system 135. In some examples, a user may elect to make their individual information available to aggregate data customer system 135 along with their consumption information and other information. Coupons or other offers may be provided directly to individual users in such examples.

Figure 2:
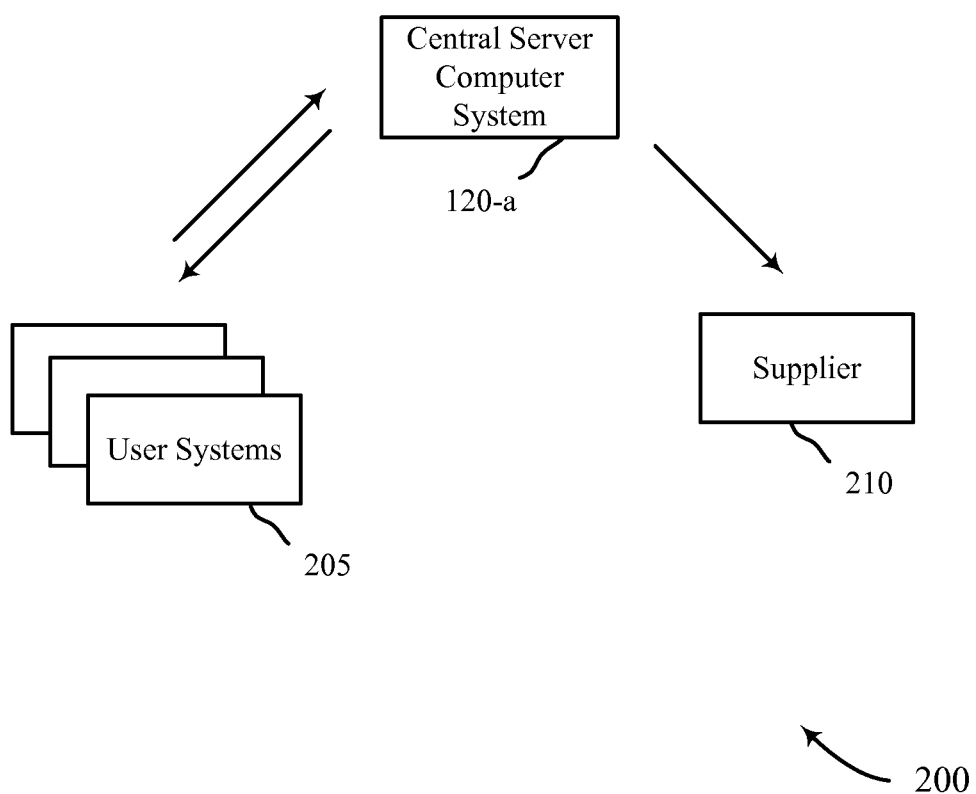
FIG. 2 shows another block diagram of an alternative example of a system of the disclosure.

With reference now to FIG. 2, an example of a system 200 that uses consumable item identification and quantity data is described. Consumption-related information from a number of user systems 205 may be provided to central server computer system 120-a. User systems 205 may be an example of user systems 105 of FIG. 1. Central server computer system 120-a collects the information and provides data to a supplier 210. Supplier 210 may be a user of an aggregate data customer system 135 of FIG. 1, for example. Supplier 210 may receive information related to one or more particular consumable items and make supply chain adjustments based on the data.

For example, similarly as described above, supplier 210 may provide consumable items to a particular geographic region, or to multiple geographic regions. If data provided by central server computer system 120-a indicate that user systems 205 in a particular geographic area have relatively high quantities of an item, and that user systems in a different geographic area have relatively low quantities of the item, the supplier 210 may elect to divert additional amounts of the item to the geographic area having relatively low quantities of the item in anticipation of increased demand in that area. In some examples, users of user systems 205 may elect to allow personally identifying information be provided to supplier 210. The supplier 210 may then use this personally identifying information, along with the consumable items and consumption-related information, to provide directed advertising or coupons to a particular user. In another example, a user may consume a relatively large amount of milk, and a supplier may provide that user with coupons or advertising related to milk in an effort to bring that user to one of the supplier's stores. In other examples, a supplier 210 may send a notice to a user that a particular item is running low, along with a coupon. In still further examples, a user of a user system 205 may enter into a replenishment agreement with supplier 210 to automatically replenish one or more consumable items when a quantity of that item drops below a certain threshold. Such thresholds may be set or adjusted by the user, and/or may be based on historical consumption patterns of the user (e.g., higher quantities of butter being used during holiday seasons).

In other examples, users of user systems 205 may elect to provide certain information related to user demographics, hobbies, activities, and/or interests. Supplier 210 may receive this information, along with the consumable items and consumption-related information, to provide directed advertising or coupons in particular locations or media known to be popular with such individuals, or at times during which such individuals are known to have increased consumption of particular items. For example, if a group of users have identified themselves as runners, consumable items and consumption-related information for that group of users may be used to identify items that may be worthwhile to advertise in locations, television shows, or publications that are known to be popular with runners. Of course, consumable item and associated consumption-related information may be used for numerous different purposes, and the examples described herein are provided for illustration and discussion only, and are not intended to limit the broad aspects of the disclosure in any way.

Figure 3:
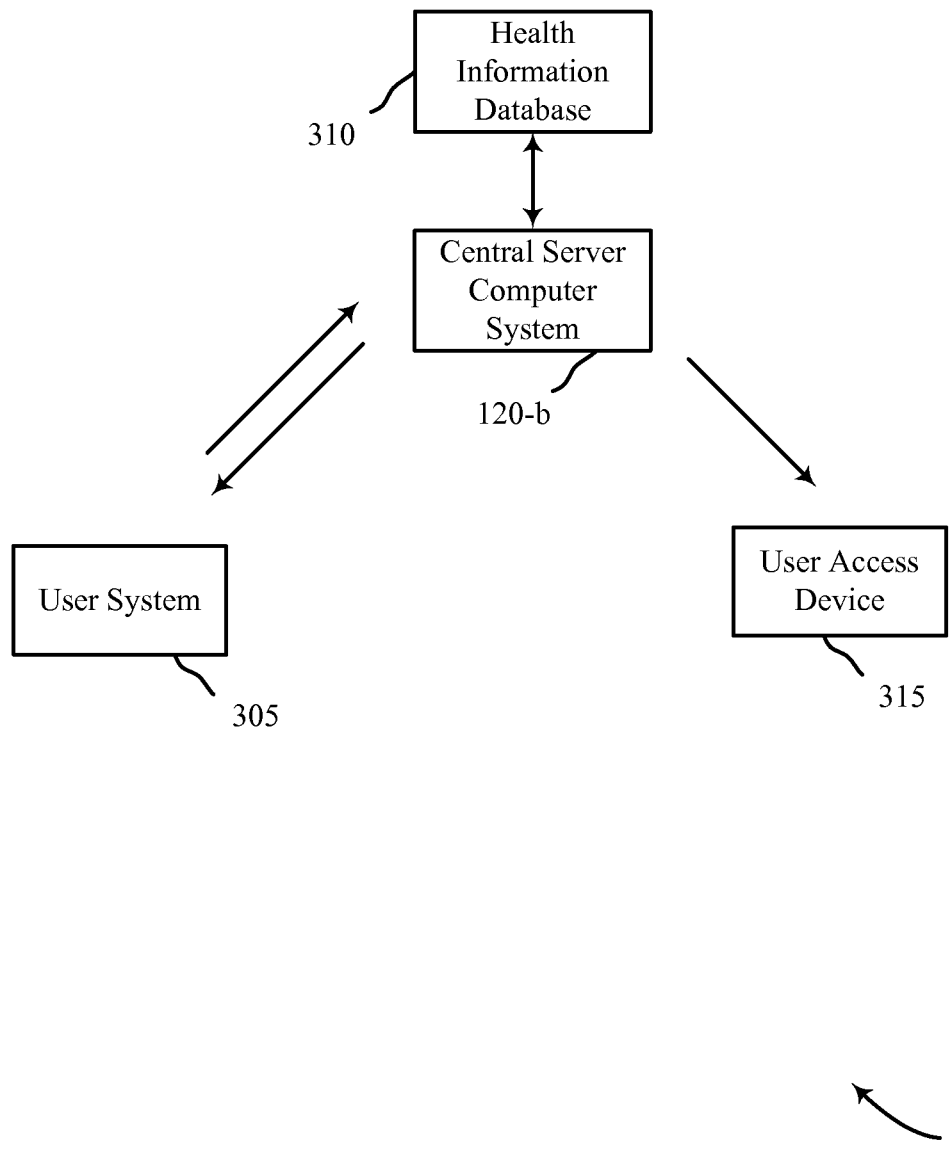
FIG. 3 shows another block diagram yet another alternative example of a system of the disclosure.

With reference now to FIG. 3, an example of a system 300 that uses consumable item identification and quantity data in health-related applications is described. Consumption-related information from a user system 305, in this example, is provided to central server computer system 120-a. User system 305 may be an example of a user system 105 of FIG. 1. Central server computer system 120-b collects the information and accesses a health information database 310. Health information database 310 may include data related to, for example, contents of different consumable items that may be evaluated to determine health advice for one or more users associated with the user system 305. For example, central server computer system 120-b may track food consumption history for a user of user system 305. The food consumed by the user may be evaluated, using health information database 310, to determine if the user has a balanced diet, for example. Other examples include monitoring of aggregate consumption of different substances, such as sodium or vitamin C, and/or other substances that may have an impact on the overall health or well-being of the user. The time of consumption may also be monitored, to determine if the user has any habits that may have an impact of the user's health, such as late-night snacking. The health information database 310 may be used to provide health-related information to a user access device 315. Such health-related information may include alerts about consumption levels, suggested recipes for a balanced diet, and relevant coupons and deals, for example.

In one example, consumption of medication may be monitored to assist with verification that a user is taking prescribed medications according to their prescription. In such an example, a medication container may have a tag, such as an RFID tag, that is identified by a weight sensing surface, with a weight monitored to verify that the weight of the item is decreasing according to the prescription. Thus, if a user is prescribed a high blood pressure medication, the medication may be provided in, or transferred to, a container having a tag. The container may be placed on a weight sensing surface of the user system 305, and identified as containing a particular quantity of the blood pressure medication. The quantity of medication in the container is monitored, and differences in quantity over time is correlated to the expected differences in quantity according to the prescription for the medication. In the event that differences in quantity are different than expected, indicating that the medication may not be being consumed as prescribed, an alert may be provided to the user, a family member, and/or a health care provider. In other examples, a prescription may be automatically re-ordered when a quantity associated with an item containing the prescribed drops below a certain level. Continuing with the previous example, the blood pressure medication may be automatically re-ordered when the quantity information indicates that fewer than a selectable number of days of the medication remain (e.g., fewer than seven days of medication assuming the medication is consumed according to the prescription). If a particular prescription is not eligible for any refills without physician approval, the system may send a notification to the user, a family member, and/or a health care provider indicating that physician approval is required. In some examples, the user system 305 may access a user's calendar and an appointment scheduler for the health care provider and propose a day and time for a physician office visit.

One input to the user system 305 may be a subsystem having one or more weight sensing surfaces, such as described above, that provides real-time, or near-real-time, quantity information about individual items consumed by the user. Other inputs could be services that track and report user body weight, and/or services that track other consumption such as through analyzing credit card statements or dining checks/receipts, for example. In one example, a service may provide consumption information based on information and/or photos of food items consumed by the user that are input using the user's mobile device. In this example, a user access device 315 may include an application that allows the user to enter information related to the user's meals, and/or take and send photos of meals. This information may be provided to the central server computer system 120-b, and health information database 310. Health information database 310, in various examples, includes data related to nutritional information in consumed foods, along with target consumption levels of various substances. Central server computer system 120-b may query the health information database 310 to determine values associated with the user that are outside of the target ranges and provide one or more of the noted alerts, suggested recipes, and coupons to the user access device 315. User access device 315 may be a user interface associated with user system, a separate access device, a mobile device such as device 130 of FIG. 1, and the like. In some examples, a report is provided to the user through email or other electronic delivery, as well as to the user's health care provider. In some examples, users may receive discounts in health-related products or insurance based on consumption patterns, with the central server computer system 120-b and health information database 310 providing information related to a particular user's consumption to determine if the user qualifies for such discounts. As will be readily apparent to one of skill in the art, consumption-related information may be used for numerous different health-related purposes, and the examples described herein are provided for illustration and discussion only, and are not intended to limit the broad aspects of the disclosure in any way.

Figure 4:
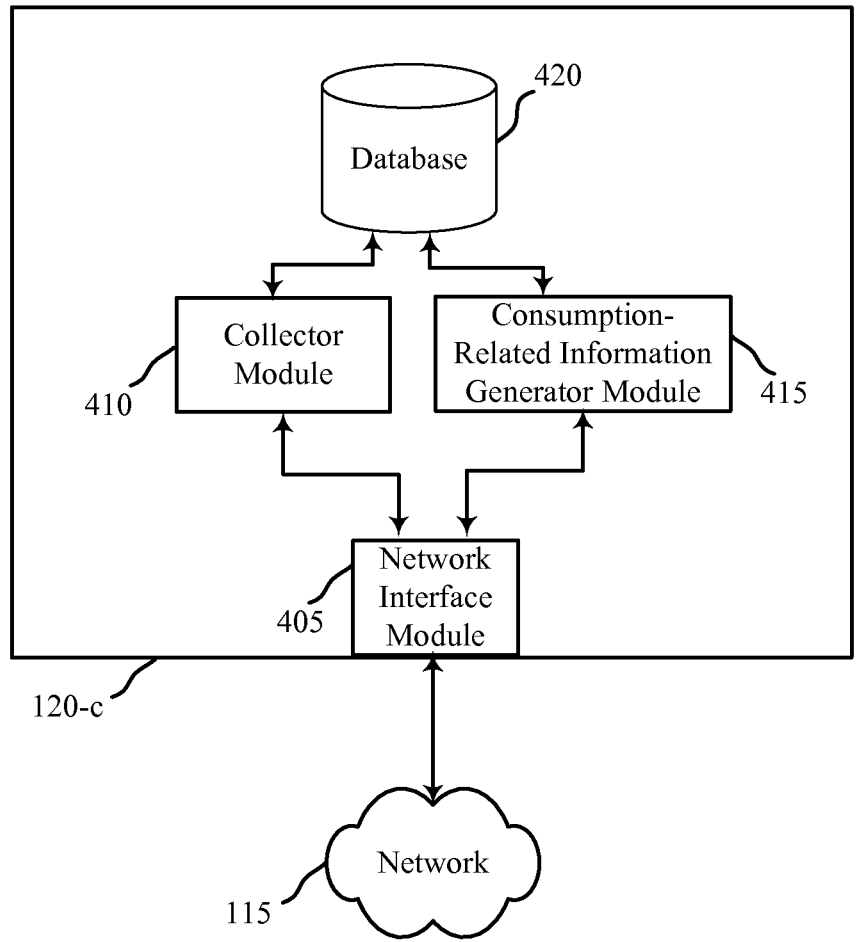
FIG. 4 shows a block diagram of an example of a central server computer system.

With reference now to FIG. 4, an example of a central server computer system 120-c is described. A network interface module 405 provides an interconnection between components of the central server computer system 120-c and the network 115. A collector module 410 receives identification and quantity data for one or more consumable items over network interface 405 and network 115 from a plurality of remote weight sensing surfaces and determines a consumption metric for the one or more consumable items. A consumption-related information generator module 415 generates consumption-related information based on the consumption metric. A database 420 is coupled with the collector module 410 and consumption-related information generator module 415 and stores data related to consumable items and quantities, which may be used by collector module 410 and consumption-related information generator module 415 to determine, for example, consumption information for an item based on weight differences for the item over time. The consumption metric may be determined based on an average rate of depletion of a consumable item across a number of replenishments of the consumable item, with information related to such history stored in database 420. In some examples, the consumption-related information generator module 415 provides a replenishment notice to a user indicating that one or more consumable items are depleted or approaching depletion. The consumption metric in such a case may include a rate of consumption for a consumable item, and the consumption-related information generator module 415 determines, based on the rate of consumption, that the consumable item is forecast to be depleted within a preset time period, and generates the replenishment notice. In some examples, the collector module determines an aggregate consumption metric for the one or more consumable items based on the received information from a group of users, similarly as described above, which may be used by the consumption-related information generator module to provide information such as described above related to advertising and/or supply chain distribution information for use in providing sufficient supply of consumable items for the group of users, for example.

The consumption-related information generator module 415 may provide recipes based on the consumption metric for the one or more consumable items, or health advice for a user, similarly as described above. Recipes may be provided that would allow a user to effectively use items that are perishable and are approaching an expiration date. In some examples, recipes are provided that seek to achieve a balanced diet for the user, in which case historical consumption may be evaluated for use in determining foods that should be eaten to achieve a balanced diet. Such recipes may be accompanied with a list of additional items that are needed to prepare the meal(s) in the recipe, which a user may use as a shopping or food delivery list. The health advice may include, for example, a warning indicating that consumption of one or more consumable items exceeds a predetermined difference from a target consumption threshold. For example, if the user is consuming foods that are high in sodium, the health advice may include a warning indicating that recent sodium consumption has exceeded a threshold level, along with one or more suggested low-sodium recipes based on available items of the user. In other examples, the consumption-related information generator module 415 may provide a coupon to a user for one or more consumable items consumed by the first user, or may provide a directed advertisement to the user based on the consumption metric for a consumable item.

Figure 5:
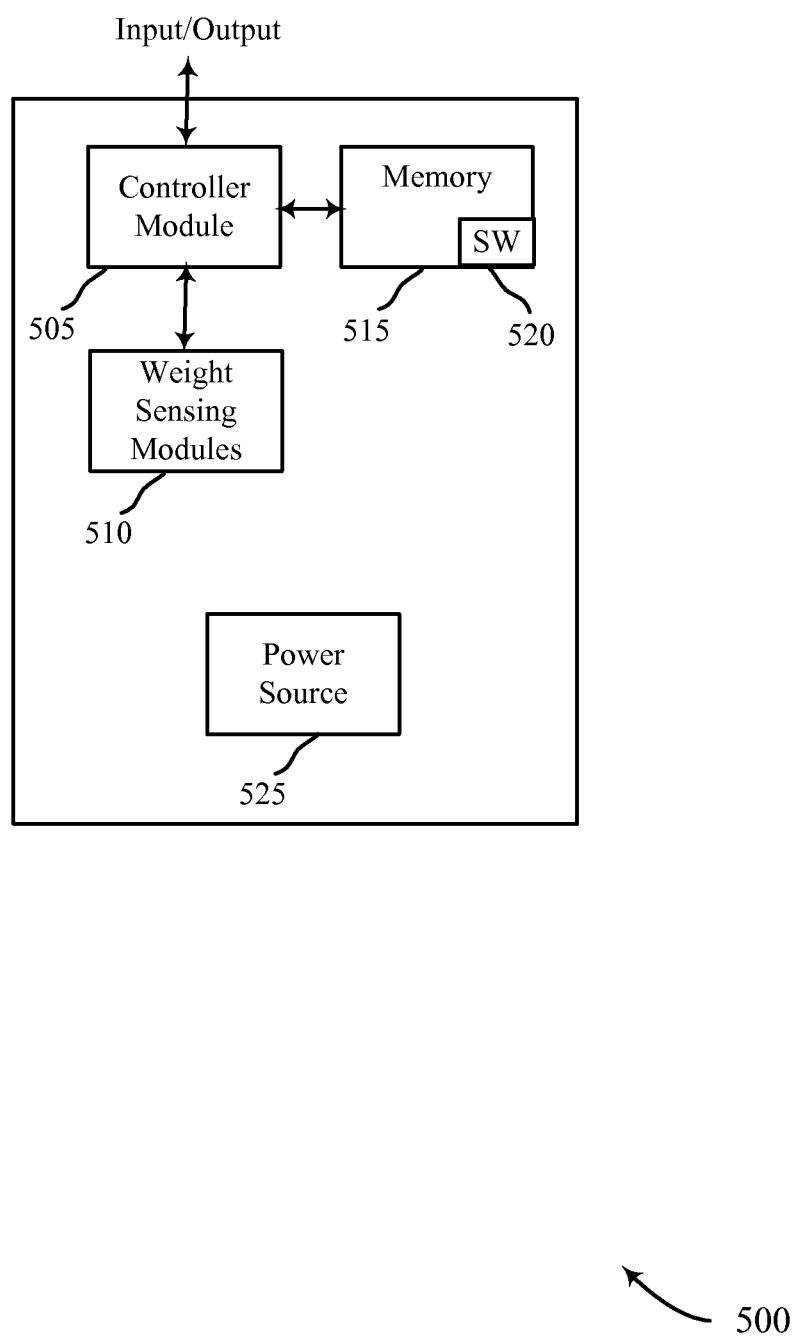
FIG. 5 shows a block diagram of an example of a user system.

With reference now to FIG. 5, a block diagram illustration of a user system 500 is described for an exemplary implementation. User system 500 may be an example of user system 110 and associated weight sensing surface(s) 115 of FIG. 1. In this example, a controller module 505 provides input and output from the system 500, such as through a wired or wireless network interface, and in some cases an associated user interface. The controller module 505 may contain a microprocessor capable of executing software algorithms. Weight sensing modules 510 may provide identification of consumable items along with associated weight information to the controller module 505. Weight sensing module 510 may be an example of weight sensing surface 115 of FIG. 1.

A memory 515 may include random access memory (RAM) and read-only memory (ROM), and store computer-readable, computer-executable software code 520 containing instructions that are configured to, when executed (or when compiled and executed), cause the controller 505 to perform various functions described herein (e.g., determine weight and identification information of consumable items, etc.). A power source 525 may include a connection to a alternating current power input and provide power to the components of system 500. The controller module 505 obtains information from the weight sensing modules 510, which may be provided to an external system (such as central server computer system 120 of FIG. 1) through an input/output. In examples where the input/output includes a user interface, the controller 505 may receive consumption-related information, such as described above, and provide the consumption-related information to the user interface. In some examples, the controller 505 is configured to read the weight of items, and control the RF antennas associated with weight sensing modules 510 to determine the location and identification of consumable items located on one or more weight sensing surfaces. The components of the user system 500 may, individually or collectively, be implemented with one or more Application Specific Integrated Circuits (ASICs) adapted to perform some or all of the applicable functions in hardware. Each of the noted modules may be a means for performing one or more functions related to operation of the user system 500.

Figure 6:
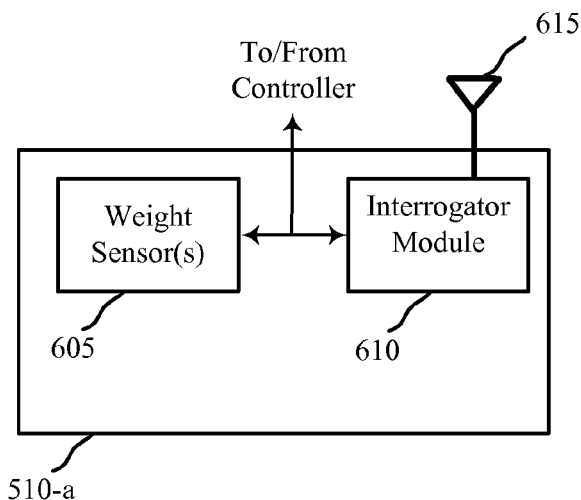
FIG. 6 shows a block diagram of an example of a weight sensing module.

With reference now to FIG. 6, a block diagram of a weight sensing module 510-*a* of an example is discussed. In this example, weight sensing module 510-*a* includes one or more weight sensors 605, and an interrogator module 610. Interrogator module 610 may be an RFID interrogator and includes an antenna 615 that is energized to transmit signals to RFID tags on consumable items that may be placed on the weight sensing module 510-*a*, and receive signals from RFID tags in response to the transmitted signals.

Figure 7:
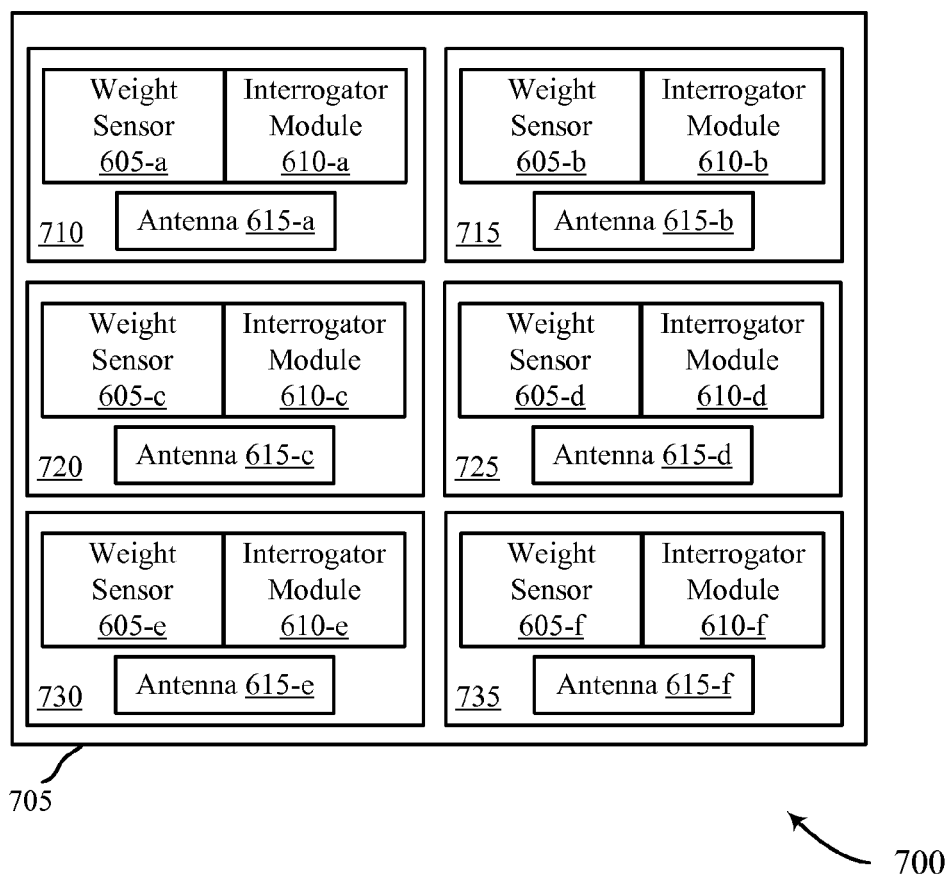
FIG. 7 shows a block diagram of an example of a grid of weight sensing modules.

In some examples, such as illustrated in block diagram 700 of FIG. 7, a number of weight sensing modules are incorporated into a weight sensing surface 705. Weight sensing modules 710-735 may include weight sensing components such as piezoelectric devices that output a voltage that is proportional to the weight of an item located on the piezoelectric device. Other weight sensors may be used, such as surface pressure sensors, MEMS-based weight sensing surfaces, electrical sensors, mechanical sensors, electro-mechanical sensors, or combinations thereof, as will be recognized by one of skill in the art. The weight sensing surface 705, in this example, is arranged in a grid pattern with a number of weight sensing modules 710-735. Each weight sensing module 710-735 includes a weight sensor 605, interrogator module 610, and antenna 615. The weight sensing surface 705, in an example, is made up of a film constructed of two layers, with interrogator modules 610-*a* through 610-*f*, and associated antennas 615-*a* through 615-*f* located in the bottom "communication layer" of surface 705, and weight sensors 605-*a* through 605-*f* located in the top layer of surface 705. As mentioned, weight sensing modules 710-735 may be arranged in an array, with each antenna 615-*a* through 615-*f* able to individually to emit an RF signal. In some examples, the power transmitted and received by the antennas 615-*a* through 615-*f* is low enough that only items located directly on or adjacent to an antenna 615 will be able to be interrogated. In such a manner, the item and its weight may be matched. In cases where an antenna 615 receives signals from more than one item, a signal strength may be used to determine the item that is closest to the interrogator, and thus the item located on that particular weight sensing module 710-735. In some examples, a single controller is coupled with each antenna 615 in the grid, and in such cases a separate interrogator module 610 may not be required for each weight sending module 710-735. The components of weight sensing surface 705 may, individually or collectively, be implemented with one or more Application Specific Integrated Circuits (ASICs) adapted to perform some or all of the applicable functions in hardware. Each of the noted modules may be a means for performing one or more functions related to operation of the surface 705.

Figure 8:
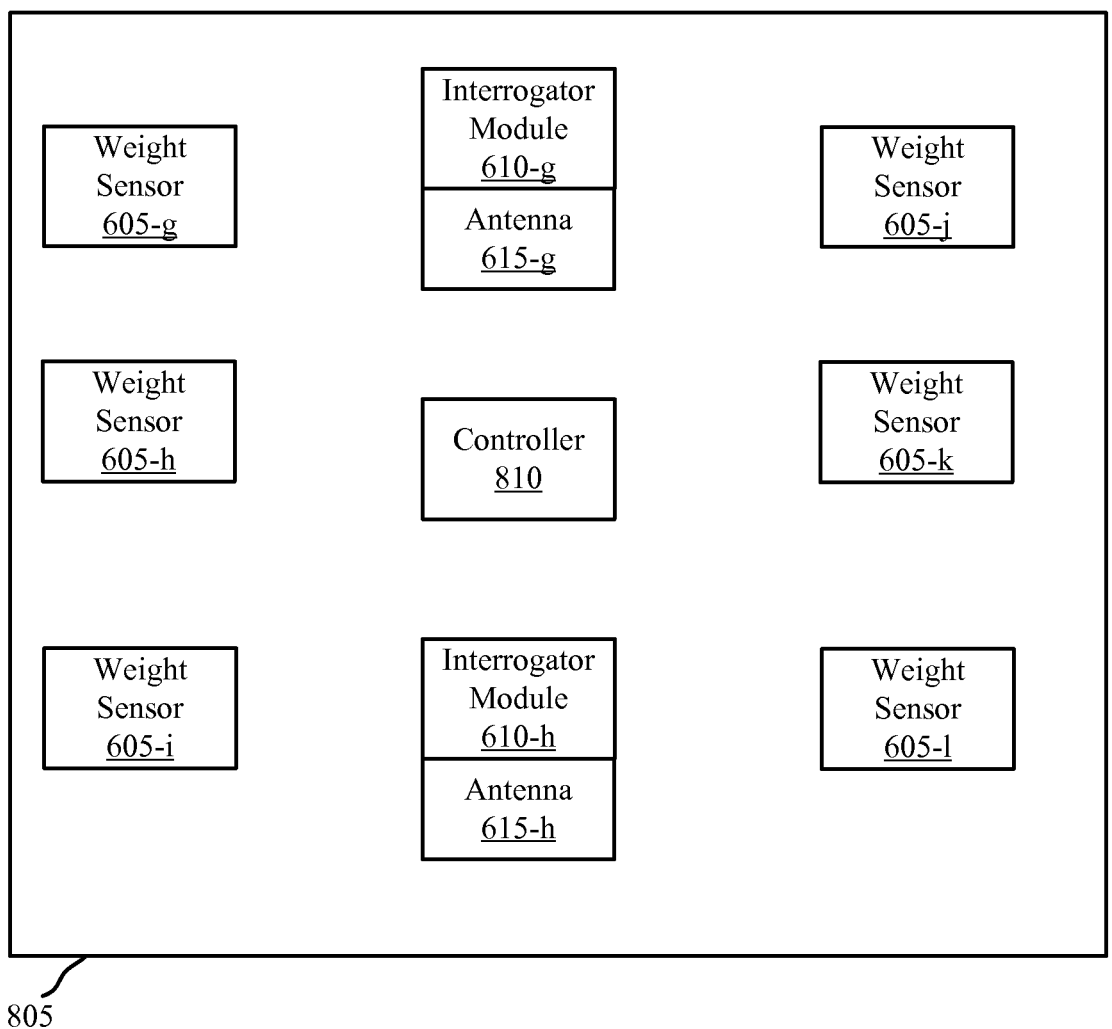
FIG. 8 shows another block diagram of an example of a grid of weight sensing modules.

In other examples, locations of items may be determined through signal strengths from RFID tags that are received by two or more interrogator antennas. An example of such a system 800 is illustrated in FIG. 8. In this example, a weight sensing surface 805 is provided that includes a grid of weight sensors 605-g through 605-l, and that includes two interrogator modules 610-g and 610-h which have associated antennas 615-g and 615-h. Weight of items placed on the portion of surface 805 associated with a particular weight sensor 605-g through 605-l, may be provided to controller 810. Controller 810 may be in communication with controller module 505 of FIG. 5, in an example. In other examples, the functions of controller 810 and interrogator modules 610-g and 610-h may be performed by controller module 505 of FIG. 5. Interrogator modules 610-g and 610-h energize antennas 615-g and 615-h to interrogate RFID tags on items that are placed on surface 805. The interrogator modules 610-g and 610-h receive signals from the RFID tags and provide the received signals to controller 810. The relative signal strengths provided by the interrogator modules 610-g and 610-h are evaluated by controller 810 to determine a location of the associated item on the surface 805. This location is matched with the weight determined by the weight sensor 605 of that location to provide weight and identification information for consumable items placed on the surface. The location, weight, and identification for items may be stored, and provided to a user of system 800. In some examples, location of an item may be identified to a user through illuminating an indicator, such as an LED incorporated into the weight sensing surface 805 at or near the location of an item of interest.

Figure 9:
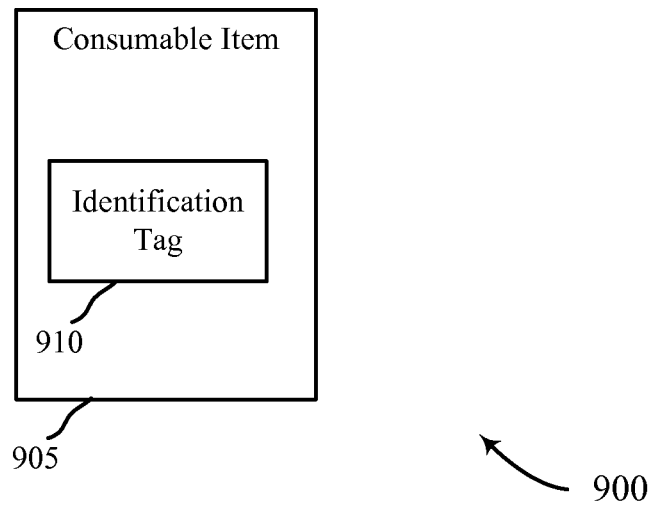
FIG. 9 shows a block diagram of an example of consumable item.

With reference now to FIG. 9, an example of a consumable item 900 is described. In this example, consumable item 900 includes a container 905 that may hold consumable material, such as a food product. An identification tag 910 provides an identification of the consumable item. In one example, the identification tag 910 includes an RFID tag that outputs a unique identification associated with the consumable item 900. Such RFID tags are well known, and many consumer products are provided with such RFID tags for inventory tracking purposes, etc. While RFID tags and interrogators are discussed in several examples, it will be understood that other identification technologies may be used, such as optical bar code technologies. The identification from the identification tag 910 is read by an interrogator, and provided to a controller that may match the identification with quantity data, such as weight data provided from a weight sensing surface as described herein.

Figure 10:
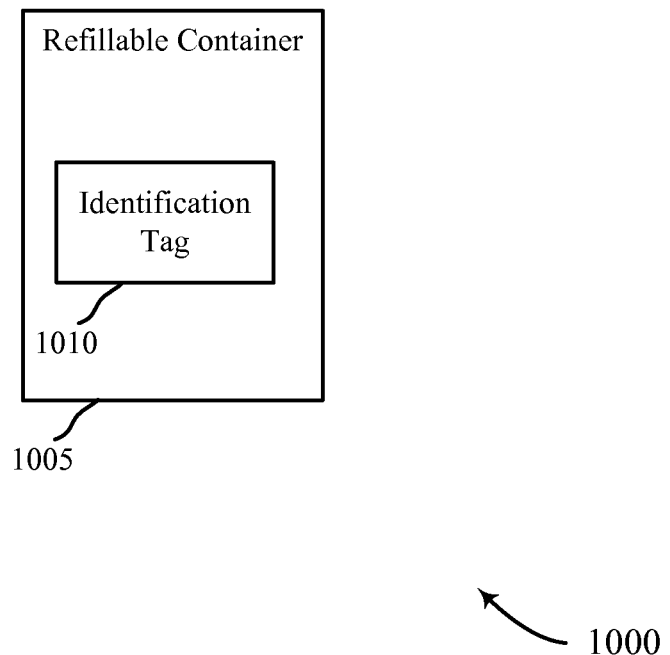
FIG. 10 shows a block diagram of an example of refillable container.

In other examples, refillable containers may be provided that are usable with systems such as described herein. An example of a refillable container system 1000 is provided in FIG. 10. In this example, a container 1005 includes an identification tag 1010. Identification tag 1010 provides an identification of the consumable item, which may be programmed via a user interface in the user system to identify a particular item that is contained in the container 1005. For example, a user may put leftover food into a container, and place the container on a weight sensing surface. An interface associated with the system may identify the item on the weight sensing surface as a refillable container, and prompt the user to enter information related to the leftover food that is in the container, such as an identification of the food, and a date by which the food should be consumed or discarded. In some examples, the identification tag may be programmed through a wireless connection to an external system, such as user system 500 of FIG. 5 for example. In such a case, a user may input information related to the contents of the container 1005 into the system user interface and the system may transmit the information to the identification tag 1010, such as through near field communication or other wireless communication. The identification tag 1010 then, when interrogated, may provide the information to the interrogating system. In other examples, the identification tag 1010 is not programmable, and information related to the contents of the container is stored in the user system memory.

Figure 11:
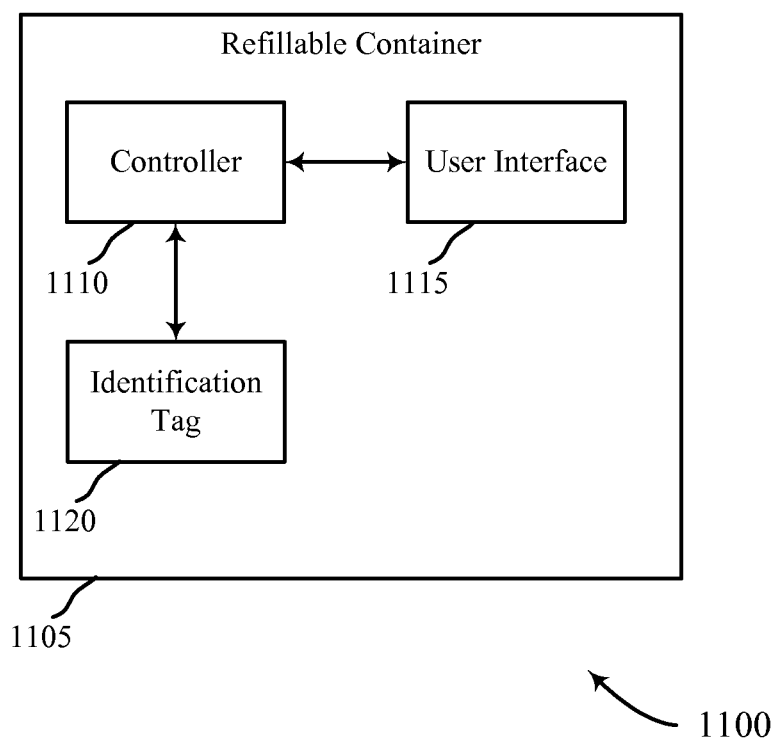
FIG. 11 shows a block diagram of an example of a programmable container.

In another example, illustrated in FIG. 11, a container system 1100 may be programmed to include information related to contents of the container. In this example, a refillable container 1105 includes a controller 1110, user interface 1115, and identification tag 1120. In this example, controller 1110 may include a memory and processor that operates to receive user input from user interface 1115 to identify a consumable item that has been placed in the refillable container 1105, along with related information, such as an identification of the consumable item, and a date by which the item should be consumed or discarded. The controller 1110, in some examples, may wirelessly receive information about the consumable item that has been placed in the refillable container 1105, along with related information, thus allowing programming of the container 1105 through either the user interface 1115 or through an external system interface such as described above with respect to FIG. 10.

Figure 12:
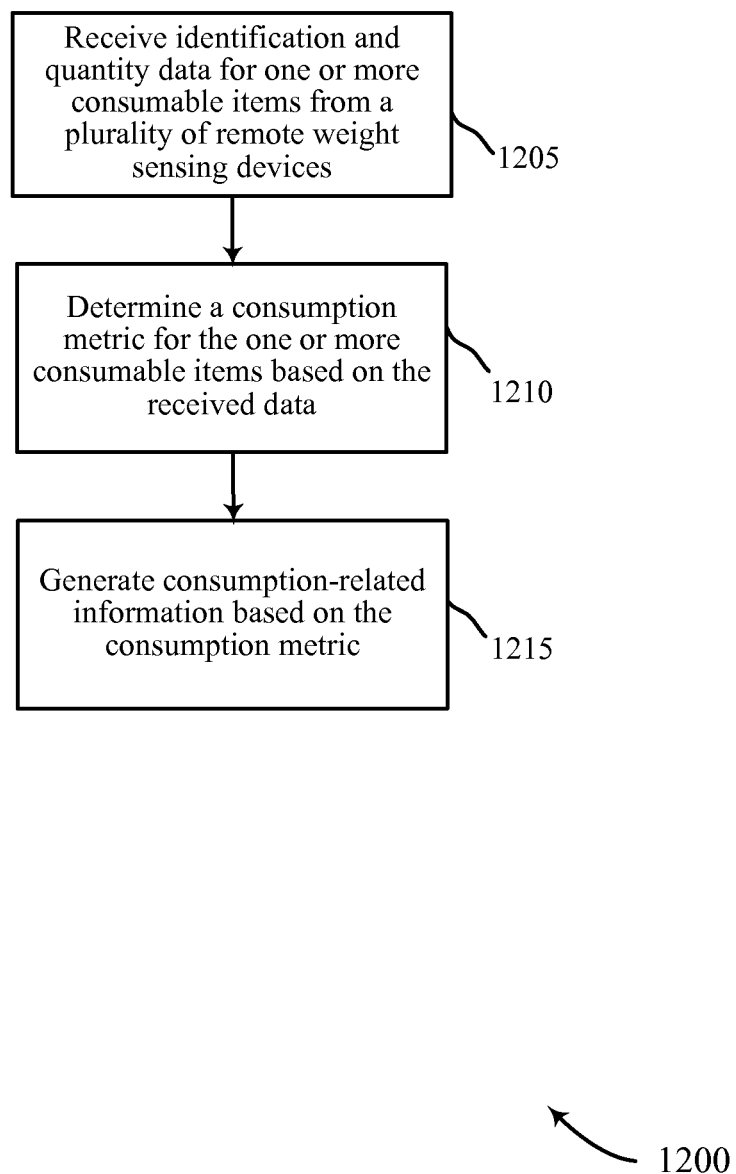
FIG. 12 is a flowchart of a method for identifying items and quantity data and generating consumption-related information.

With reference now to FIG. 12, a method 1200 for generating a consumption-related metric are described. The method 1200 may, for example, be performed by a central server computer system or user system of FIGS. 1 through 8, or using any combination of the devices described for these figures. Initially, at block 1205, identification and quantity data for one or more consumable items is received from a plurality of remote weight sensing devices. Such data may be received from a weight sensing surface such as described above. For example, a container of eggs may be placed on a weight sensing surface. The weight sensing surface may interrogate a tag on the egg container that identifies the container as containing eggs. A weight associated with the container is determined, with the weight and identification information received according to block 1205. In some examples, a time is associated with the weight and identification information that may be used to provide information related to the time of consumption. A consumption metric is determined for the one or more consumable items based on the received data, as noted at block 1210. Continuing with the above example, the received weight and identification data may be compared to one or more previous weights of that particular item, and a difference in weight used to determine a quantity of the item that has been consumed. In the example of the container having eggs, a quantity of eggs consumed for one or more time periods may be determined as the consumption metric. Consumption-related information is generated, at block 1215, based on the consumption metric. Such consumption-related information may include information such as described above, including aggregate consumption-related information, and health-related information. For example, aggregate consumption-related information may include information for a group of users in a geographic area, in a social network, with a common set of interests, etc. Health-related information may include warnings that consumption of certain substances is above or below a target threshold, medication information, and/or recipe information such as described above.

Figure 13:
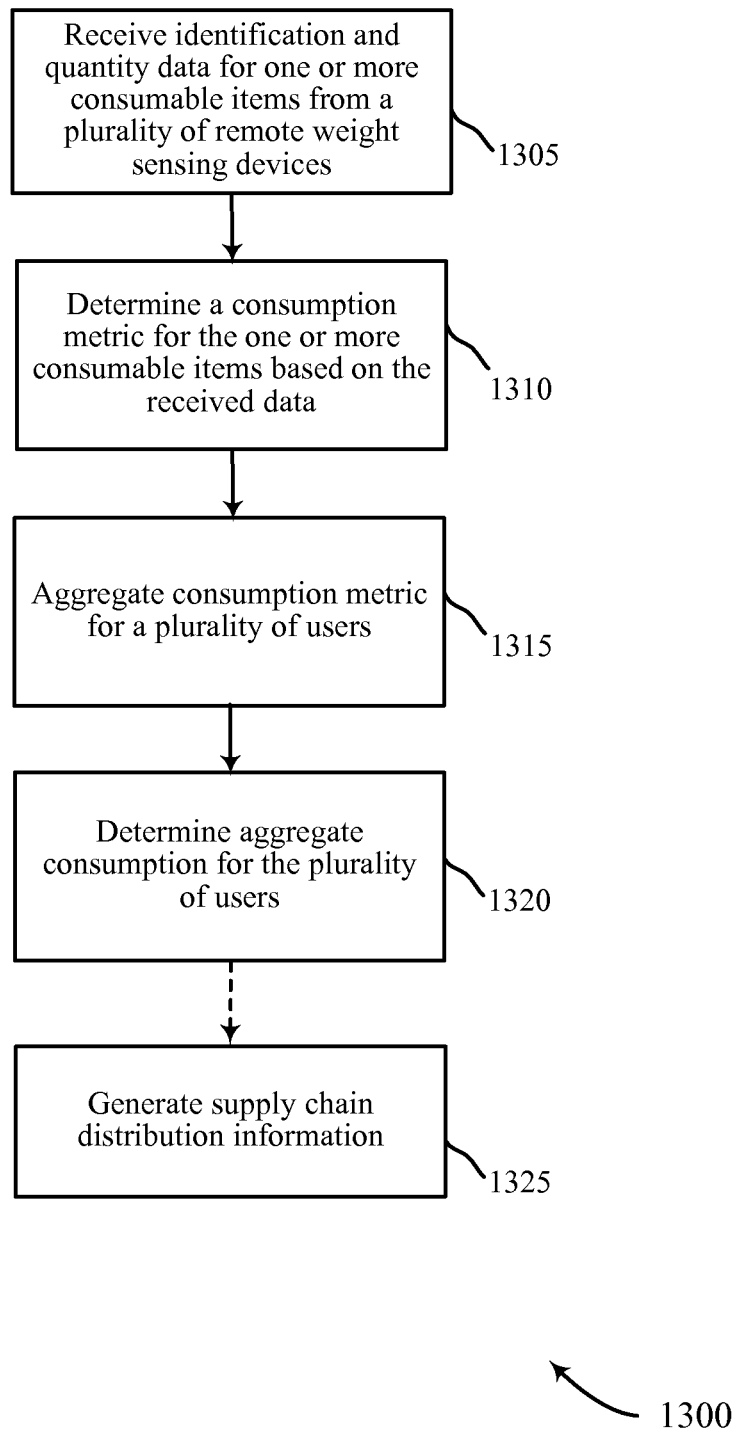
FIG. 13 is a flowchart of another method for identifying items and quantity data and determining aggregate consumption related to the items.

FIG. 13 illustrates a method 1300 for determining aggregate consumption information. The method 1300 may, for example, be performed by a central server computer system or user system of FIGS. 1 through 8, or using any combination of the devices described for these figures. Initially, at block 1305, identification and quantity data for one or more consumable items is received from a plurality of remote weight sensing devices. A consumption metric is determined for the one or more consumable items based on the received data, as noted at block 1310. The consumption metric for a plurality of users is aggregated, according to block 1315. The plurality of users may be users in a particular geographic area, users with one or more common interests, or users of a particular demographic, for example. Aggregate consumption for the plurality of users is determined at block 1320. Such aggregate consumption information may be used for any of a number of applications, such as market research, public health, supply chain management, to name but a few examples. In one example, according to optional block 1325, supply chain distribution information is generated. Such supply chain distribution information may include, similarly as described above, an indication that demand in a particular geographic area or for a particular group of users is likely to be increased or decreased in the near future based on the aggregate consumption for the plurality of users.

Figure 14:
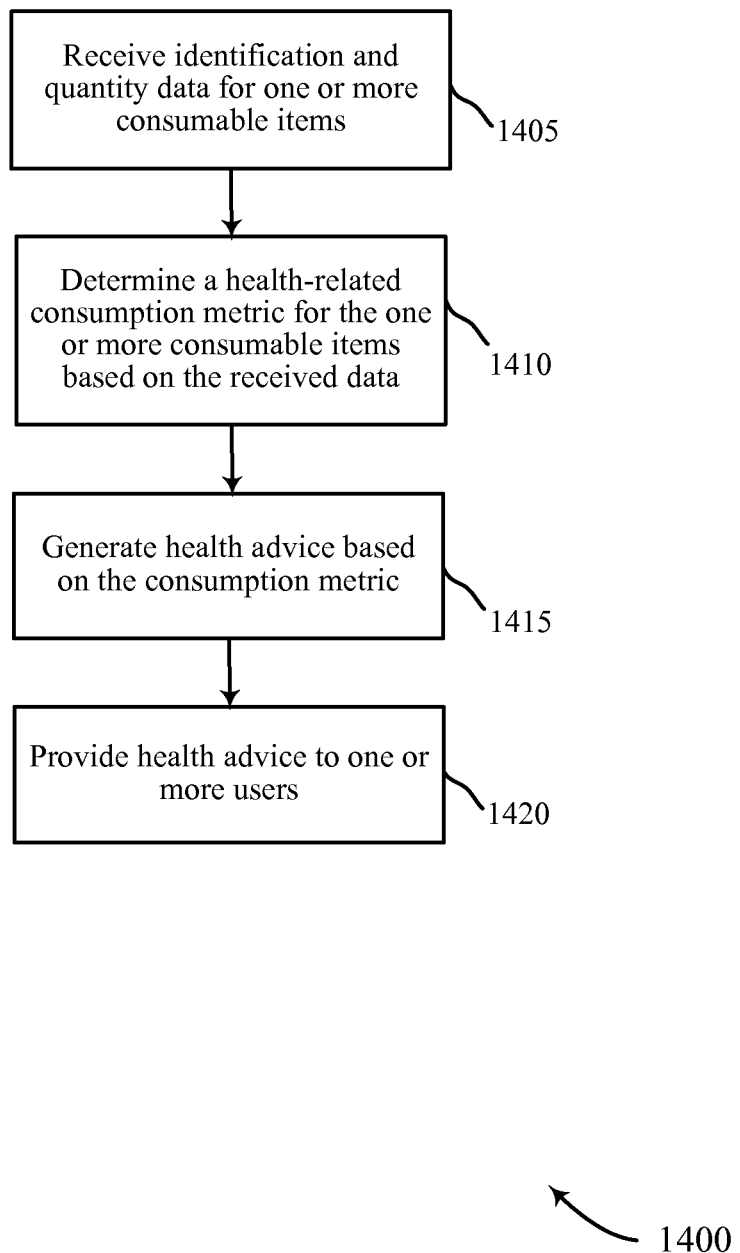
FIG. 14 is a flowchart of a method for generating health advice based on consumption data.

With reference now to FIG. 14, a method 1400 for providing health advice is described. The method 1400 may, for example, be performed by a central server computer system, health information database, or user system of FIGS. 1 through 8, or using any combination of the devices described for these figures. Initially, at block 1405, identification and quantity data for one or more consumable items is received. A health-related consumption metric is determined for the one or more consumable items based on the received data, according to block 1410. Such a health-related consumption metric may include, for example, information related to a balanced diet, information related to intake of various substances, information related to the time of consumption of various items, and/or information related to quantities of prescribed medication that are present. At block 1415, health advice is generated based on the consumption metric. Such health advice may include, for example, recipes that may promote a balanced diet or adjust for intake quantities of a substance (e.g., increased whole grains when whole grain intake is below a target threshold). Health advice may also include an alarm or notification that intake of an item or substance is above or below a threshold level (e.g., sodium intake is too high, medications are not being taken properly, etc.). Finally, at block 1420, health advice is provided to one or more users. Such health advice may be provided, for example, to a user of the system, a health care professional, and/or a family member of the user. In some other examples, the health-related consumption metric may be used to qualify a user for discounted medical insurance premiums or discounted medical services.

Figure 15:
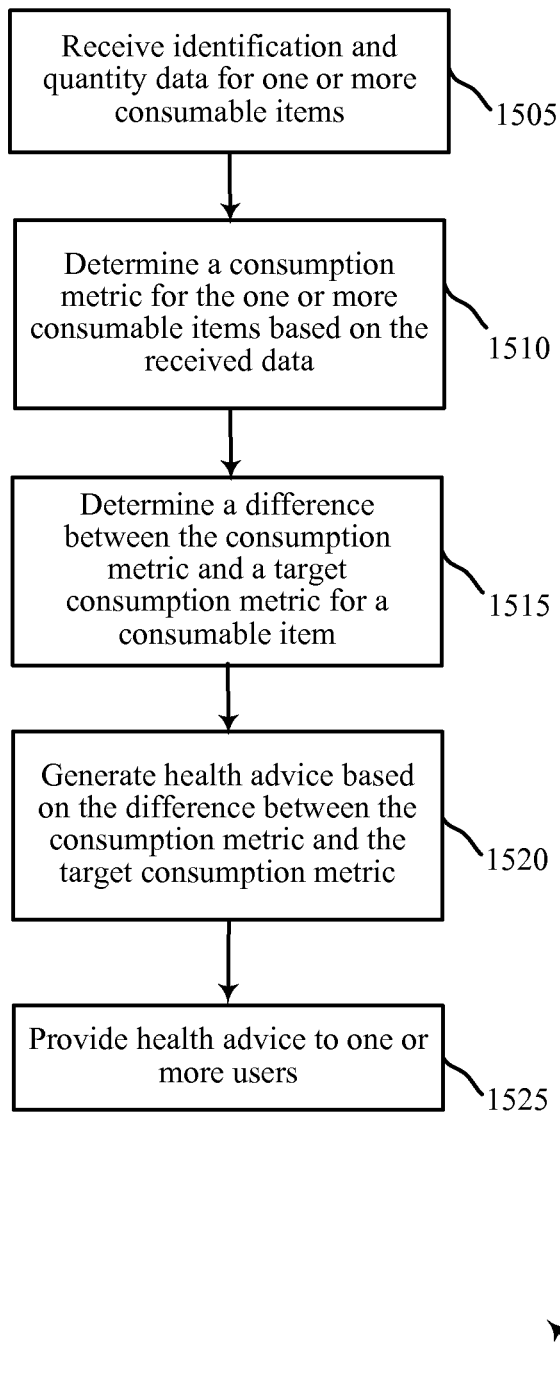
FIG. 15 is a flowchart of another method for generating health advice based on consumption data.

With reference now to FIG. 15, an alternative method 1500 for providing health advice is described. The method 1500 may, for example, be performed by a central server computer system, health information database, or user system of FIGS. 1 through 8, or using any combination of the devices described for these figures. Initially, at block 1505, identification and quantity data is received for one or more consumable items. At block 1510, a consumption metric is determined for the one or more consumable items based on the received data. A difference between the consumption metric and a target consumption metric for a consumable item is determined at block 1515. For example, the consumption metric may be a sodium intake for a user of the system that is based on the sodium content of foods that the user has consumed over a set time period. A target sodium consumption metric may be established for the user based on, for example, the user's age and weight, and the difference determined based on the actual amount of sodium consumed and the target sodium consumption metric. The target consumption metric may also be based on times of consumption of items, such as a target to consume fewer than a certain number of calories after a certain time of day to help reduce late-night snacking, for example. Health advice is generated based on the difference between the consumption metric and the target consumption metric, at block 1520. At block 1525, health advice is provided to one or more users. Similarly as described above, health advice may include, for example, recipes that may promote a balanced diet or adjust for intake quantities of a substance (e.g., decreased sodium when sodium intake is above a target threshold), or advice to take a nutritional supplement. Health advice may also include one or more recipes that compensate for differences between the consumption metric and target consumption metric. In some embodiments, health advice may be provided to third parties other than a user of the system, such as a family member or health care provider.

Figure 16:
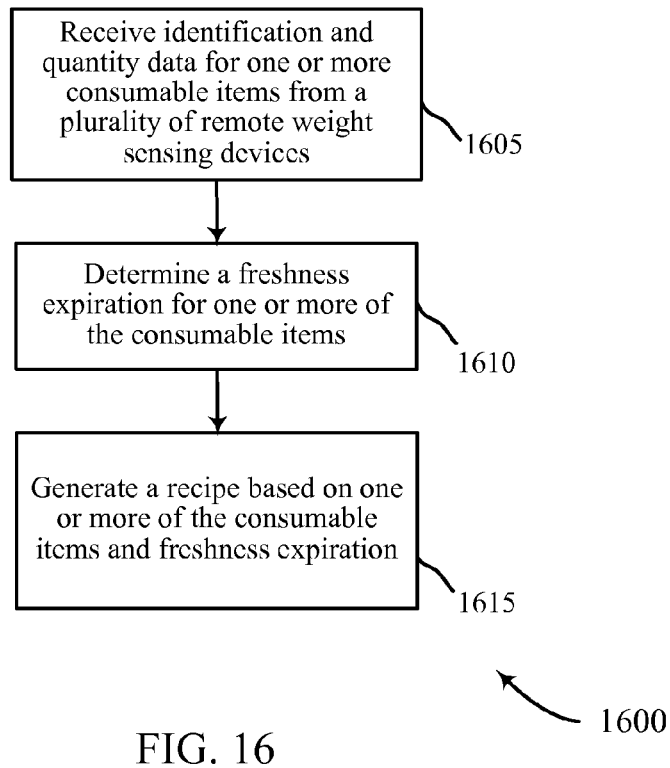
FIG. 16 is a flowchart of a method for providing recipe information based on item identification.

Still other examples provide for efficient use of consumable items that may be present in a user system. One such example, described with reference to FIG. 16, provides a method 1600 to generate recipes to use items that may be at or approaching the end of their useful life. The method 1600 may, for example, be performed by a central server computer system, or user system of FIGS. 1 through 8, or using any combination of the devices described for these figures. Initially, at block 1605, identification and quantity data is received for one or more consumable items from a plurality of remote weight sensing devices. At block 1610, a freshness expiration for one or more of the consumable items is determined. In such cases, a consumable item may have a known freshness period, and the system may record the date on which an item is placed in the system, with freshness expiration based on such a date and the known freshness period. In other examples, the identification of the consumable item may include freshness information and a date by which the item should be consumed or discarded. For example, an RFID tag on a container of food may be programmed with an identification of the food and an expiration date. At block 1615, a recipe is generated based on one or more of the consumable items and freshness expiration. In such a manner, waste may be reduced by identifying products that may be in danger of spoiling and providing a convenient way to consume the items. The recipe may also include a listing of additional items needed that are not present in the user system, thus providing a convenient shopping list for the user to obtain additional items needed for the recipe. In some examples, a number of different recipes are provided to give the user various options, one or more of which may be selected based on the current desires or mood of the user. In other examples, the user may input a desired type of meal that is desired (e.g., an Italian meal), and recipes generated based on the input and consumable items that are present in the user's system.

Figure 17:
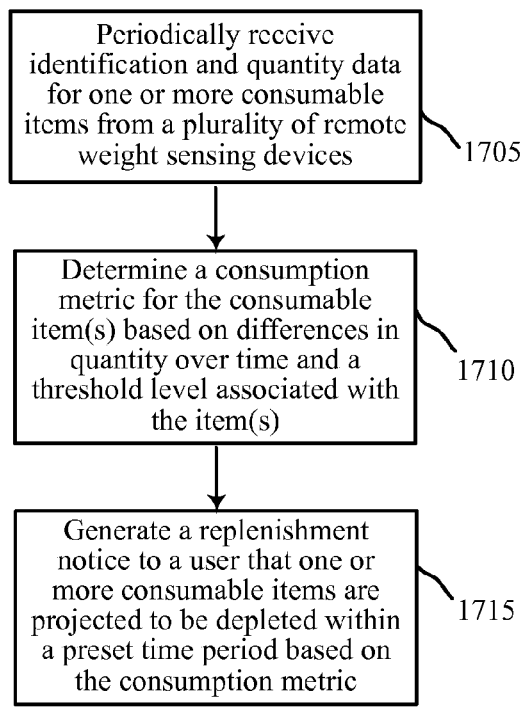
FIG. 17 is a flowchart of a method for providing replenishment information based on item identification and quantity data.

With reference now to FIG. 17, a method 1700 for providing notice to a user that an item is running low is described. The method 1700 may, for example, be performed by a central server computer system, or user system of FIGS. 1 through 8, or using any combination of the devices described for these figures. Initially, at block 1705, identification and quantity data is received for one or more consumable items. A consumption metric is determined for the consumable item(s) based on differences in quantity over time and a threshold level associated with the item(s), according to block 1710. A replenishment notice is generated to a user indicating that one or more consumable items are projected to be depleted within a preset time period based on the consumption metric, as indicated at block 1715. Thus, a user may be notified that an item is almost empty. In some examples, a user may set thresholds for generating such notices, in order to help insure that an item will not be empty. In other examples, a user may set a threshold based on the tolerance for being without an item. For instance, if a user has a low tolerance for being without milk, a threshold may be set relatively conservatively to generate a replenishment notice in advance of running out of milk. Of course, various other thresholds may be set in accordance with user preferences and tolerances, as will be readily apparent to one skilled in the art. In some examples, the system may adaptively set thresholds based on a user's history. For example, a system may monitor when milk is replenished by a user and determine a threshold and a user's tolerance for being without milk based on historical data. If, in this example, a user is very rarely without milk and historically replenishes milk when 20% of the existing milk remains, the threshold may be set to generate a replenishment notice when the level of milk approaches 20%. Replenishment notices may also be provided, for example, when a product is approaching an expiration date, and/or when a manufacturer issues a recall for the item.

The detailed description set forth above in connection with the appended drawings describes exemplary implementations and does not represent the only examples that may be implemented or that are within the scope of the claims. The term "exemplary" used throughout this description means "serving as an example, instance, or illustration," and not "preferred" or "advantageous over other embodiments." The detailed description includes specific details for the purpose of providing an understanding of the described techniques. These techniques, however, may be practiced without these specific details. In some instances, well-known structures and devices are shown in block diagram form in order to avoid obscuring the concepts as described.

Information and signals may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

The various illustrative blocks and modules described in connection with the disclosure herein may be implemented or performed with a general-purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor may be a microprocessor, but in the alternative, the processor may be any conventional processor, controller, microcontroller, or state machine. A processor may also be implemented as a combination of computing devices, e.g., a combination of a DSP and a microprocessor, multiple microprocessors, one or more microprocessors in conjunction with a DSP core, or any other such configuration.

The functions described herein may be implemented in hardware, software executed by a processor, firmware, or any combination thereof. If implemented in software executed by a processor, the functions may be stored on or transmitted over as one or more instructions or code on a computer-readable medium. Other examples and implementations are within the scope and spirit of the disclosure and appended claims. For example, due to the nature of software, functions described above can be implemented using software executed by a processor, hardware, firmware, hardwiring, or combinations of any of these. Features implementing functions may also be physically located at various positions, including being distributed such that portions of functions are implemented at different physical locations. Also, as used herein, including in the claims, "or" as used in a list of items prefaced by "at least one of" indicates a disjunctive list such that, for example, a list of "at least one of A, B, or C" means A or B or C or AB or AC or BC or ABC (i.e., A and B and C).

Computer-readable media includes both computer storage media and communication media including any medium that facilitates transfer of a computer program from one place to another. A storage medium may be any available medium that can be accessed by a general purpose or special purpose computer. By way of example, and not limitation, computer-readable media can comprise RAM, ROM, EEPROM, CD-ROM or other optical disk storage, magnetic disk storage or other magnetic storage devices, or any other medium that can be used to carry or store desired program code means in the form of instructions or data structures and that can be accessed by a general-purpose or special-purpose computer, or a general-purpose or special-purpose processor. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, include compact disc (CD), laser disc, optical disc, digital versatile disc (DVD), floppy disk and blu-ray disc where disks usually reproduce data magnetically, while discs reproduce data optically with lasers. Combinations of the above are also included within the scope of computer-readable media.

The previous description of the disclosure is provided to enable a person skilled in the art to make or use the disclosure. Various modifications to the disclosure will be readily apparent to those skilled in the art, and the generic principles defined herein may be applied to other variations without departing from the spirit or scope of the disclosure. Throughout this disclosure the term "example" or "exemplary" indicates an example or instance and does not imply or require any preference for the noted example. Thus, the disclosure is not to be limited to the examples and designs described herein but is to be accorded the widest scope consistent with the principles and novel features disclosed herein.

What is claimed is:

1. A method comprising:
   receiving, at a central computer system, identification and quantity data for one or more consumable items from a first user system remote from the central computer system, the first user system comprising one or more weight sensing devices for determining the identification and quantity data;
   determining a consumption metric for the one or more consumable items based on the received identification and quantity data;
   generating consumption-related information based on the consumption metric; and
   transmitting, from the central computer system, the consumption-related information to the first user system.

2. The method of claim 1, further comprising:
receiving, at the central computer system, additional identification and quantity data from a plurality of different user systems, each of the plurality of different user systems comprising one or more additional weight sensing devices for determining the additional identification and quantity data, and
determining an aggregate consumption metric for the one or more consumable items based on the received identification and quantity data from the first user system and the additional identification and quantity data from the plurality of different user systems.

3. The method of claim 2, wherein generating consumption-related information comprises generating supply chain distribution information for use in providing sufficient supply for replenishment of the one or more consumable items for the first user system and the plurality of different user systems.

4. The method of claim 2, wherein the first user system and the plurality of different user systems comprise user systems within one or more of: a defined geographic area, a defined demographic, a defined interest group, and a defined social network.

5. The method of claim 1, wherein the consumption-related information comprises one or more recipes based on the consumption metric for the one or more consumable items.

6. The method of claim 1, wherein the consumption-related information comprises health advice for a first user of the first user system.

7. The method of claim 6, wherein the health advice comprises a warning to the first user indicating that consumption of one or more consumable items exceeds a predetermined difference from a target threshold.

8. The method of claim 1, wherein generating consumption-related information comprises generating a coupon for a first user associated with the first user system for one or more consumable items consumed by the first user.

9. The method of claim 1, wherein generating consumption-related information comprises providing a directed advertisement to a first user associated with the first user system based on the consumption metric for one or more consumable items consumed by the first user.

10. The method of claim 1, wherein:
the receiving identification and quantity data comprises periodically receiving identification and quantity data, and
the determining the consumption metric is based on differences in quantity data over time.

11. The method of claim 1, wherein:
the receiving identification and quantity data comprises periodically receiving identification and quantity data for a first consumable item, and
the determining the consumption metric is based on a rate of depletion of the first consumable item.

12. The method of claim 11, wherein determining the consumption metric is based on an average rate of depletion of the first consumable item across a plurality of replenishments of the first consumable item.

13. The method of claim 1, wherein generating the consumption-related information based on the consumption metric comprises:
generating a replenishment notice to the first user system indicating that one or more consumable items are depleted or approaching depletion.

14. The method of claim 13, wherein generating the replenishment notice comprises:

determining that quantity data for the one or more consumable items is below a quantity threshold associated with the one or more consumable items; and
generating the replenishment notice.

15. The method of claim 13, wherein the consumption metric comprises a rate of consumption for a consumable item, and generating the replenishment notice comprises:
determining, based on the rate of consumption, that the consumable item is forecast to be depleted within a preset time period; and
generating the replenishment notice.

16. The method of claim 15, wherein the preset time period for the consumable item is selectable by the first user system.

17. An apparatus, comprising:
a collector module that receives identification and quantity data for one or more consumable items from a first user system and determines a consumption metric for the one or more consumable items based on the received identification and quantity data, the first user system comprising one or more weight sensing surfaces for determining the identification and quantity data;
a consumption-related information generator module that generates consumption-related information based on the consumption metric; and
a network interface module that transmits the consumption-related information to the first user system.

18. The apparatus of claim 17, wherein the collector module determines an aggregate consumption metric for the one or more consumable items based on the received identification and quantity data from the first user system and from additional identification and quantity data from a plurality of different user systems.

19. The apparatus of claim 18, wherein the consumption-related information generator module provides supply chain distribution information for use in providing sufficient supply of the one or more consumable items for the first user system and the plurality of different user systems based on the aggregate consumption metric.

20. The apparatus of claim 18, wherein the first user system and the plurality of different user systems comprise user systems within one or more of: a defined geographic area, a defined demographic, a defined interest group, and a defined social network.

21. The apparatus of claim 17, wherein the consumption-related information comprises one or more recipes based on the consumption metric for the one or more consumable items.

22. The apparatus of claim 17, wherein the consumption-related information comprises health advice for a first user of the first user system.

23. The apparatus of claim 22, wherein the health advice comprises a warning indicating that consumption of one or more consumable items exceeds a predetermined difference from a target threshold.

24. The apparatus of claim 17, wherein the consumption-related information comprises a coupon for a first user associated with the first user system for one or more consumable items consumed by the first user.

25. The apparatus of claim 17, wherein the consumption-related information comprises a directed advertisement to a first user associated with the first user system based on the consumption metric for one or more consumable items consumed by the first user.

26. The apparatus of claim 17, wherein:
the collector module receives periodic updates of the identification and quantity data for the one or more consumable items, and determines the consumption metric based on a rate of depletion of the one or more consumable items.

27. The apparatus of claim 26, wherein the consumption metric is determined based on an average rate of depletion of one or more first consumable items across a plurality of replenishments of the one or more consumable items.

28. The apparatus of claim 17, wherein the network interface module provides a replenishment notice to the first user system indicating that one or more consumable items are depleted or approaching depletion.

29. The apparatus of claim 28, wherein the consumption metric comprises a rate of consumption for a consumable item, and the consumption-related information generator module determines, based on the rate of consumption, that the consumable item is forecast to be depleted within a preset time period, and generates the replenishment notice.

30. A system comprising:
  means for receiving identification and quantity data for one or more consumable items from a first user system remote from the means for receiving, the first user system comprising one or more weight sensing means for determining the identification and quantity data;
  means for determining a consumption metric for the one or more consumable items based on the received identification and quantity data;
  means for generating consumption-related information based on the consumption metric; and
  means for transmitting the consumption-related information to the first user system.

31. The system of claim 30, further comprising:
  means for receiving additional identification and quantity data from a plurality of different user systems, each of the plurality of different user systems comprising one or more additional weight sensing means for determining the additional identification and quantity data, and
  means for determining an aggregate consumption metric for the one or more consumable items based on the received identification and quantity data from the first user system and the additional identification and quantity data from the plurality of different user systems.

32. The system of claim 31, wherein the means for generating consumption-related information comprises:
  means for generating supply chain distribution information for use in providing sufficient supply for replenishment of the one or more consumable items for the first user system and the plurality of different user systems.

33. The system of claim 31, wherein the first user system and the plurality of different user systems comprise user systems within one or more of: a defined geographic area, a defined demographic, a defined interest group, and a defined social network.

34. The system of claim 30, wherein the consumption-related information comprises one or more recipes based on the consumption metric for the one or more consumable items.

35. The system of claim 30, wherein the consumption-related information comprises health advice for a first user of the first user system.

36. The system of claim 35, wherein the health advice comprises a warning to the first user indicating that consumption of one or more consumable items exceeds a predetermined difference from a target threshold.

37. The system of claim 30, wherein:
  the means for receiving identification and quantity data comprises means for periodically receiving identification and quantity data, and
  the means for determining the consumption metric comprise means for determining the consumption metric based on differences in quantity data over time.

38. A non-transitory computer readable medium storing code executable by a processor, the code comprising:
  code for receiving, at a central computer system, identification and quantity data for one or more consumable items from a first user system remote from the central computer system, the first user system comprising one or more weight sensing devices for determining the identification and quantity data;
  code for determining a consumption metric for the one or more consumable items based on the received identification and quantity data;
  code for generating consumption-related information based on the consumption metric; and
  code for transmitting, from the central computer system, the consumption-related information to the first user system.

39. The non-transitory computer readable medium of claim 38, wherein the code further comprises:
  code for receiving, at the central computer system, additional identification and quantity data from a plurality of different user systems, each of the plurality of different user systems comprising one or more additional weight sensing devices for determining the additional identification and quantity data, and
  code for determining an aggregate consumption metric for the one or more consumable items based on the received identification and quantity data from the first user system and the additional identification and quantity data from the plurality of different user systems.

40. The non-transitory computer readable medium of claim 39, wherein the code for generating consumption-related information comprises code for generating supply chain distribution information for use in providing sufficient supply for replenishment of the one or more consumable items for the first user system and the plurality of different user systems.

41. The non-transitory computer readable medium of claim 39, wherein the first user system and the plurality of different user systems comprise user systems within one or more of: a defined geographic area, a defined demographic, a defined interest group, and a defined social network.

42. The non-transitory computer readable medium of claim 38, wherein the consumption-related information comprises one or more recipes based on the consumption metric for the one or more consumable items.

43. The non-transitory computer readable medium of claim 38, wherein the consumption-related information comprises health advice for a first user of the first user system.

44. The non-transitory computer readable medium of claim 43, wherein the health advice comprises a warning to the first user indicating that consumption of one or more consumable items exceeds a predetermined difference from a target threshold.

45. The non-transitory computer readable medium of claim 38, wherein the code for generating consumption-related information comprises code for generating a coupon for a first user associated with the first user system for one or more consumable items consumed by the first user.

46. The non-transitory computer readable medium of claim 38, wherein the code for generating consumption-related information comprises code for providing a directed advertisement to a first user associated with the first user system based on the consumption metric for one or more consumable items consumed by the first user.

47. The non-transitory computer readable medium of claim 38, wherein:
   the code for receiving identification and quantity data comprises code for periodically receiving identification and quantity data, and
   the code for determining the consumption metric comprises code for determining the consumption metric based on differences in quantity data over time.

48. The non-transitory computer readable medium of claim 38, wherein:
   the code for receiving identification and quantity data comprises code for periodically receiving identification and quantity data for a first consumable item, and
   the code for determining the consumption metric comprises code for determining the consumption metric based on a rate of depletion of the first consumable item.

* * * * *